US012751697B2

(12) United States Patent
Igarashi et al.

(10) Patent No.: US 12,751,697 B2
(45) Date of Patent: Oct. 6, 2026

(54) ULTRASOUND DIAGNOSTIC APPARATUS AND METHOD OF CONTROLLING ULTRASOUND DIAGNOSTIC APPARATUS

(71) Applicant: FUJIFILM Corporation, Tokyo (JP)

(72) Inventors: Riki Igarashi, Kanagawa (JP); Tsuyoshi Matsumoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 63 days.

(21) Appl. No.: 18/955,534

(22) Filed: Nov. 21, 2024

(65) Prior Publication Data

US 2025/0213222 A1 Jul. 3, 2025

(30) Foreign Application Priority Data

Dec. 27, 2023 (JP) ................................ 2023-220660

(51) Int. Cl.
*A61B 8/00* (2006.01)
*A61B 5/11* (2006.01)
*A61B 8/08* (2006.01)

(52) U.S. Cl.
CPC ................ *A61B 8/483* (2013.01); *A61B 5/11* (2013.01); *A61B 5/1113* (2013.01); (Continued)

(58) Field of Classification Search
CPC ......... A61B 8/483; A61B 8/085; A61B 8/461; A61B 8/5238; A61B 8/429; A61B 8/466; A61B 8/5207; A61B 8/4263
See application file for complete search history.

(56) References Cited

U.S. PATENT DOCUMENTS

2007/0299336 A1* 12/2007 Ikuma .................... A61B 5/065 600/424
2008/0281189 A1* 11/2008 Komuro ............... A61B 6/5247 600/424

(Continued)

FOREIGN PATENT DOCUMENTS

CN 112807025 A 5/2021
JP 2021-053379 A 4/2021
WO 2023/242072 A1 12/2023

OTHER PUBLICATIONS

The extended European search report issued by the European Patent Office on Apr. 30, 2025, which corresponds to European Patent Application No. 24217055.3-1122 and is related to U.S. Appl. No. 18/955,534.

*Primary Examiner* — Keith M Raymond
*Assistant Examiner* — Johnathan Maynard
(74) *Attorney, Agent, or Firm* — Studebaker Brackett PLLC

(57) ABSTRACT

Provided are an ultrasound diagnostic apparatus that enables a user to easily and accurately perform a comprehensive observation of an organ as an observation target regardless of a skill level, and a method of controlling the ultrasound diagnostic apparatus.

An ultrasound diagnostic apparatus includes: a template memory in which a plurality of organ templates are stored; a three-dimensional ultrasound image acquisition unit that acquires a three-dimensional ultrasound image of an organ by transmitting and receiving an ultrasound beam using an ultrasound probe; a template selection unit that selects one organ template from among the plurality of organ templates in accordance with a posture of a subject; and a scanning progress status output unit that specifies a scanning progress status of the ultrasound probe for the organ by performing registration between the three-dimensional ultrasound image (Continued)

acquired by the three-dimensional ultrasound image acquisition unit and the one organ template selected by the template selection unit, and outputs the specified scanning progress status.

20 Claims, 10 Drawing Sheets

(52) U.S. Cl.
CPC ........... *A61B 5/1114* (2013.01); *A61B 5/1116* (2013.01); *A61B 5/1128* (2013.01); *A61B 8/085* (2013.01); *A61B 8/461* (2013.01)

(56) References Cited

U.S. PATENT DOCUMENTS

| | | | | |
|---|---|---|---|---|
| 2012/0101388 | A1 | 4/2012 | Tripathi | |
| 2014/0163376 | A1* | 6/2014 | Caluser | G16H 30/20 600/443 |
| 2015/0182191 | A1* | 7/2015 | Caluser | A61B 8/4254 600/407 |
| 2015/0310581 | A1 | 10/2015 | Radulescu et al. | |
| 2019/0000318 | A1* | 1/2019 | Caluser | A61B 5/0073 |
| 2020/0196979 | A1* | 6/2020 | Van Heesch | A61B 8/4254 |
| 2020/0237347 | A1* | 7/2020 | De Beni | G06T 17/00 |
| 2021/0068782 | A1* | 3/2021 | Caluser | A61B 8/4245 |
| 2021/0093303 | A1* | 4/2021 | Fujisawa | A61B 8/5246 |
| 2021/0353261 | A1* | 11/2021 | Ebata | A61B 8/085 |
| 2022/0047244 | A1* | 2/2022 | Caluser | A61B 8/5207 |
| 2023/0062672 | A1 | 3/2023 | Hyun et al. | |
| 2023/0157660 | A1 | 5/2023 | Tu et al. | |

* cited by examiner

ULTRASOUND DIAGNOSTIC APPARATUS AND METHOD OF CONTROLLING ULTRASOUND DIAGNOSTIC APPARATUS

CROSS-REFERENCE TO RELATED APPLICATIONS

The present application claims priority under 35 U.S.C. § 119 to Japanese Patent Application No. 2023-220660, filed on Dec. 27, 2023. The above application is hereby expressly incorporated by reference, in its entirety, into the present application.

BACKGROUND OF THE INVENTION

1. Field of the Invention

The present invention relates to an ultrasound diagnostic apparatus used in a case of comprehensively observing an organ of a subject and a method of controlling the ultrasound diagnostic apparatus.

2. Description of the Related Art

In the related art, an ultrasound image representing a tomogram of a subject is captured by using a so-called ultrasound diagnostic apparatus, thereby observing an inside of the subject. In this case, for example, a user, such as a doctor, comprehensively observes a specific organ of the subject.

In this case, the user usually sequentially captures ultrasound images while determining a captured part of the subject by checking the captured ultrasound image, but a user having a low skill level in an observation using the ultrasound diagnostic apparatus may have difficulty in determining which part of the subject is imaged even by checking the ultrasound image. Therefore, for example, as disclosed in JP2021-053379A, a technology has been developed in which a region that has been scanned or a region that has not yet been scanned in an organ as an observation target is specified and displayed by comparing data obtained by transmitting and receiving ultrasound to and from the organ as the observation target with data representing a reference shape of the organ as the observation target.

SUMMARY OF THE INVENTION

By the way, depending on a posture of the subject, such as a so-called sitting posture or decubitus posture, the organ in the subject receives a force from a tissue in the subject, gravity, and the like, and a shape of the organ is changed. In the technology disclosed in JP2021-053379A, in a case in which the shape of the organ as the observation target is changed by the application of the force, a shape of the organ corresponding to data used as a reference does not correspond to an actual shape of the organ, so that it is not possible to specify the region that has been scanned or the region that has not yet been scanned, and it may be difficult to accurately perform the comprehensive observation of the organ depending on the skill level of the user.

The present invention has been made in order to solve such a problem in the related art, and an object of the present invention is to provide an ultrasound diagnostic apparatus that enables a user to easily and accurately perform a comprehensive observation of an organ as an observation target regardless of a skill level, and a method of controlling the ultrasound diagnostic apparatus.

With the following configuration, the above-described object can be achieved.

[1] An ultrasound diagnostic apparatus for observing an organ of a subject by performing scanning using an ultrasound probe, the ultrasound diagnostic apparatus comprising: a template memory in which a plurality of organ templates are stored; a three-dimensional ultrasound image acquisition unit that acquires a three-dimensional ultrasound image of the organ by transmitting and receiving an ultrasound beam using the ultrasound probe; a template selection unit that selects one organ template from among the plurality of organ templates in accordance with a posture of the subject; and a scanning progress status output unit that specifies a scanning progress status of the ultrasound probe for the organ by performing registration between the three-dimensional ultrasound image acquired by the three-dimensional ultrasound image acquisition unit and the one organ template selected by the template selection unit, and outputs the specified scanning progress status.

[2] The ultrasound diagnostic apparatus according to [1], in which the plurality of organ templates include organ templates corresponding to the organ in respective cases in which the subject is in a sitting posture, a decubitus posture, a ventral decubitus posture, and a lateral decubitus posture.

[3] The ultrasound diagnostic apparatus according to [1] or [2], in which each of the plurality of organ templates consists of three-dimensional data representing a contour of the organ in accordance with the posture of the subject.

[4] The ultrasound diagnostic apparatus according to [1] or [2], in which each of the plurality of organ templates consists of three-dimensional data representing a contour of the organ and an internal structure of the organ in accordance with the posture of the subject.

[5] The ultrasound diagnostic apparatus according to any one of [1] to [4], further comprising: an input device for a user to perform an input operation, in which the template selection unit selects the one organ template based on the posture of the subject designated by the user via the input device.

[6] The ultrasound diagnostic apparatus according to any one of [1] to [4], further comprising: a posture detection unit that detects the posture of the subject, in which the template selection unit selects the one organ template based on the posture of the subject detected by the posture detection unit.

[7] The ultrasound diagnostic apparatus according to [6], in which the template selection unit calculates a degree of similarity with respect to the posture of the subject detected by the posture detection unit for each of the plurality of organ templates, and selects an organ template having a highest degree of similarity as the one organ template.

[8] The ultrasound diagnostic apparatus according to [6], in which the template selection unit selects the one organ template by using a trained model that has learned an output from the posture detection unit in accordance with the posture of the subject.

[9] The ultrasound diagnostic apparatus according to any one of [6] to [8], in which the posture detection unit includes an optical camera that images the subject, and an optical image analysis unit that analyzes an optical image acquired by the optical camera, to detect the posture of the subject.

[10] The ultrasound diagnostic apparatus according to any one of [6] to [8], in which the posture detection unit includes at least one pressure sensor that is disposed on an examination table on which the subject is placed in a case in which the subject undergoes an examination, and a signal analysis unit that analyzes a detection signal acquired by the at least one pressure sensor, to detect the posture of the subject.

[11] The ultrasound diagnostic apparatus according to any one of [1] to [4], in which the template selection unit selects the one organ template based on the three-dimensional ultrasound image acquired by the three-dimensional ultrasound image acquisition unit.

[12] The ultrasound diagnostic apparatus according to [11], in which the template selection unit calculates a degree of similarity with respect to the three-dimensional ultrasound image acquired by the three-dimensional ultrasound image acquisition unit for each of the plurality of organ templates, and selects an organ template having a highest degree of similarity as the one organ template.

[13] The ultrasound diagnostic apparatus according to [11], in which the template selection unit selects the one organ template by using a trained model that has learned the three-dimensional ultrasound image of the organ in accordance with the posture of the subject.

[14] The ultrasound diagnostic apparatus according to any one of [1] to [13], further comprising: a monitor, in which the scanning progress status output unit displays the scanning progress status of the ultrasound probe on the monitor.

[15] The ultrasound diagnostic apparatus according to [14], in which the scanning progress status output unit displays a region that has been scanned using the ultrasound probe or a region that has not yet been scanned using the ultrasound probe on the monitor as the scanning progress status.

[16] The ultrasound diagnostic apparatus according to any one of [1] to [14], in which the scanning progress status output unit divides the organ into a plurality of sections, quantifies the scanning progress status of the ultrasound probe in each of the plurality of sections, and outputs the quantified scanning progress status.

[17] The ultrasound diagnostic apparatus according to [16], in which the scanning progress status output unit outputs a section in which further scanning using the ultrasound probe is recommended among the plurality of sections based on the quantified scanning progress statuses of the ultrasound probe in the plurality of sections.

[18]A method of controlling an ultrasound diagnostic apparatus for observing an organ of a subject by performing scanning using an ultrasound probe, the method comprising: storing a plurality of organ templates in a template memory; acquiring a three-dimensional ultrasound image of the organ by transmitting and receiving an ultrasound beam using the ultrasound probe; selecting one organ template from among the plurality of organ templates in accordance with a posture of the subject; and specifying a scanning progress status of the ultrasound probe for the organ by performing registration between the acquired three-dimensional ultrasound image and the selected one organ template, and outputting the specified scanning progress status.

In the present invention, the ultrasound diagnostic apparatus comprises: the template memory in which the plurality of organ templates are stored; the three-dimensional ultrasound image acquisition unit that acquires the three-dimensional ultrasound image of the organ by transmitting and receiving the ultrasound beam using the ultrasound probe; the template selection unit that selects the one organ template from among the plurality of organ templates in accordance with the posture of the subject; and the scanning progress status output unit that specifies the scanning progress status of the ultrasound probe for the organ by performing the registration between the three-dimensional ultrasound image acquired by the three-dimensional ultrasound image acquisition unit and the one organ template selected by the template selection unit, and outputs the specified scanning progress status, and thus it is possible for the user to easily and accurately perform the comprehensive observation of the organ as the observation target regardless of the skill level.

DESCRIPTION OF THE PREFERRED EMBODIMENTS

Hereinafter, embodiments of the present invention will be described on the basis of the accompanying drawings.

The configuration requirements are described later based on a representative embodiment of the present invention, but the present invention is not limited to such an embodiment.

In the present specification, a numerical range represented by "to" means a range including numerical values described before and after "to" as a lower limit value and an upper limit value.

In the present specification, "the same" includes an error range generally allowed in the technical field.

Embodiment 1

Figure 1:
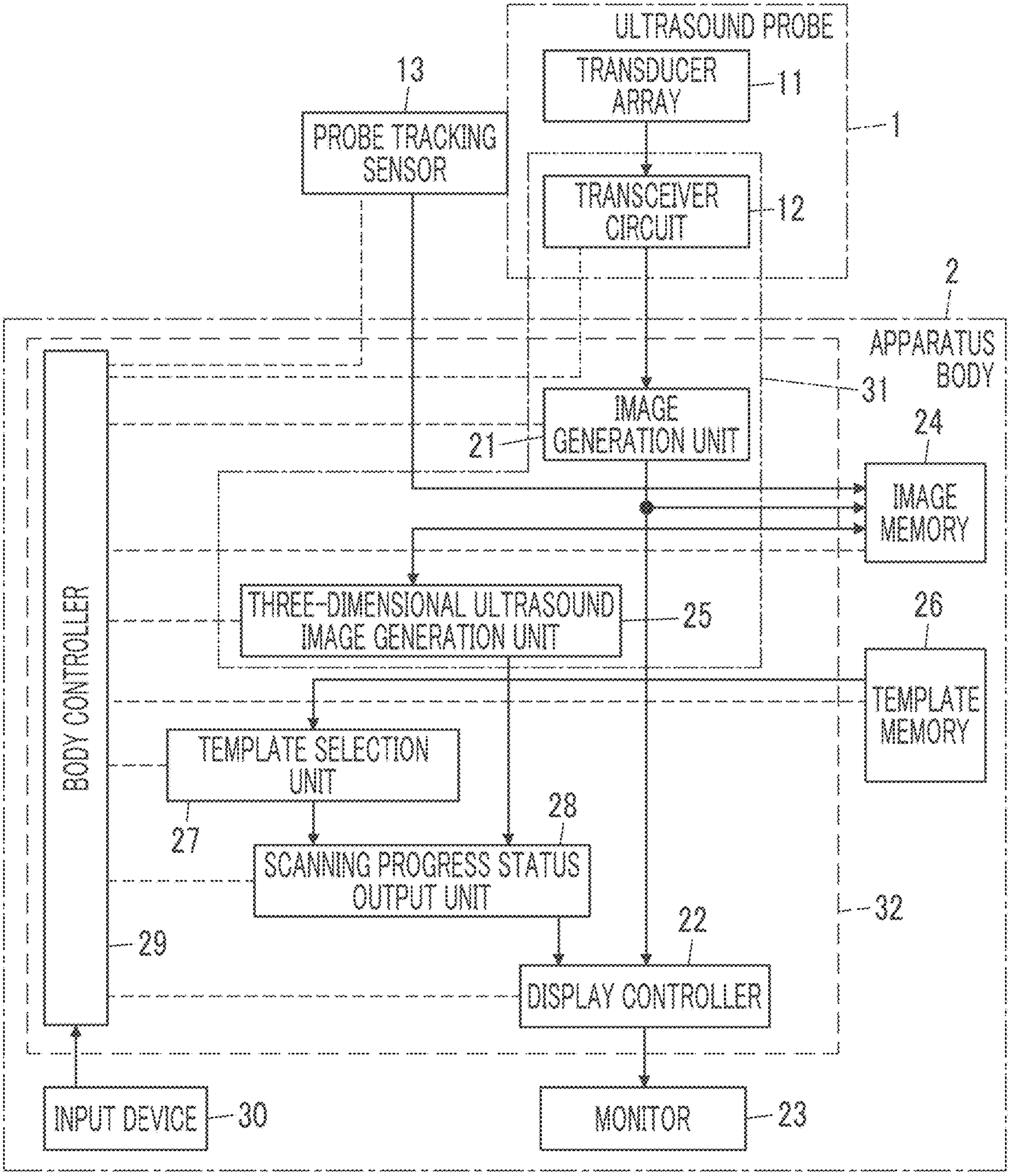
FIG. 1 is a block diagram showing a configuration of an ultrasound diagnostic apparatus according to Embodiment 1 of the present invention.

FIG. 1 shows a configuration of an ultrasound diagnostic apparatus according to Embodiment 1 of the present invention. The ultrasound diagnostic apparatus comprises an ultrasound probe 1, and an apparatus body 2 connected to the ultrasound probe 1. The ultrasound probe 1 and the apparatus body 2 are connected to each other via so-called wired communication or so-called wireless communication.

The ultrasound probe 1 includes a transducer array 11. A transceiver circuit 12 is connected to the transducer array 11. The ultrasound probe 1 includes a probe tracking sensor 13. The probe tracking sensor 13 may be incorporated in the ultrasound probe 1 or attached to a housing of the ultrasound probe 1. In addition, in a case in which a sensor device, such as a so-called optical sensor, that measures the ultrasound probe 1 from the outside is used as the probe tracking sensor 13, the probe tracking sensor 13 may be disposed at a position away from the ultrasound probe 1.

The apparatus body 2 includes an image generation unit 21 connected to the transceiver circuit 12 of the ultrasound probe 1. A display controller 22 and a monitor 23 are sequentially connected to the image generation unit 21. An image memory 24 is connected to the image generation unit 21. A three-dimensional ultrasound image generation unit 25 is connected to the image memory 24. In addition, the apparatus body 2 comprises a template memory 26. A template selection unit 27 is connected to the template memory 26. Further, a scanning progress status output unit 28 is connected to the three-dimensional ultrasound image generation unit 25 and the template selection unit 27. The scanning progress status output unit 28 is connected to the display controller 22. Further, a body controller 29 is connected to the probe tracking sensor 13, the transceiver circuit 12, the image generation unit 21, the display controller 22, the image memory 24, the three-dimensional ultrasound image generation unit 25, the template memory 26, the template selection unit 27, and the scanning progress status output unit 28. An input device 30 is connected to the body controller 29.

The transceiver circuit 12, the image generation unit 21, and the three-dimensional ultrasound image generation unit 25 constitute a three-dimensional ultrasound image acquisition unit 31. In addition, the image generation unit 21, the display controller 22, the three-dimensional ultrasound image generation unit 25, the template selection unit 27, the scanning progress status output unit 28, and the body controller 29 constitute a processor 32 for the apparatus body 2.

The transducer array 11 of the ultrasound probe 1 includes a plurality of ultrasound transducers arranged one-dimensionally or two-dimensionally. In response to a drive signal supplied from the transceiver circuit 12, each of the ultrasound transducers transmits ultrasound and receives an ultrasound echo from a subject to output a signal based on the ultrasound echo. For example, each ultrasound transducer is configured by forming electrodes at both ends of a piezoelectric material consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), and the like.

The three-dimensional ultrasound image acquisition unit 31 configured by the transceiver circuit 12, the image generation unit 21, and the three-dimensional ultrasound image generation unit 25 acquires a three-dimensional ultrasound image of an organ of the subject by transmitting and receiving an ultrasound beam using the ultrasound probe 1. A method of acquiring the three-dimensional ultrasound image will be described later.

Figure 2:
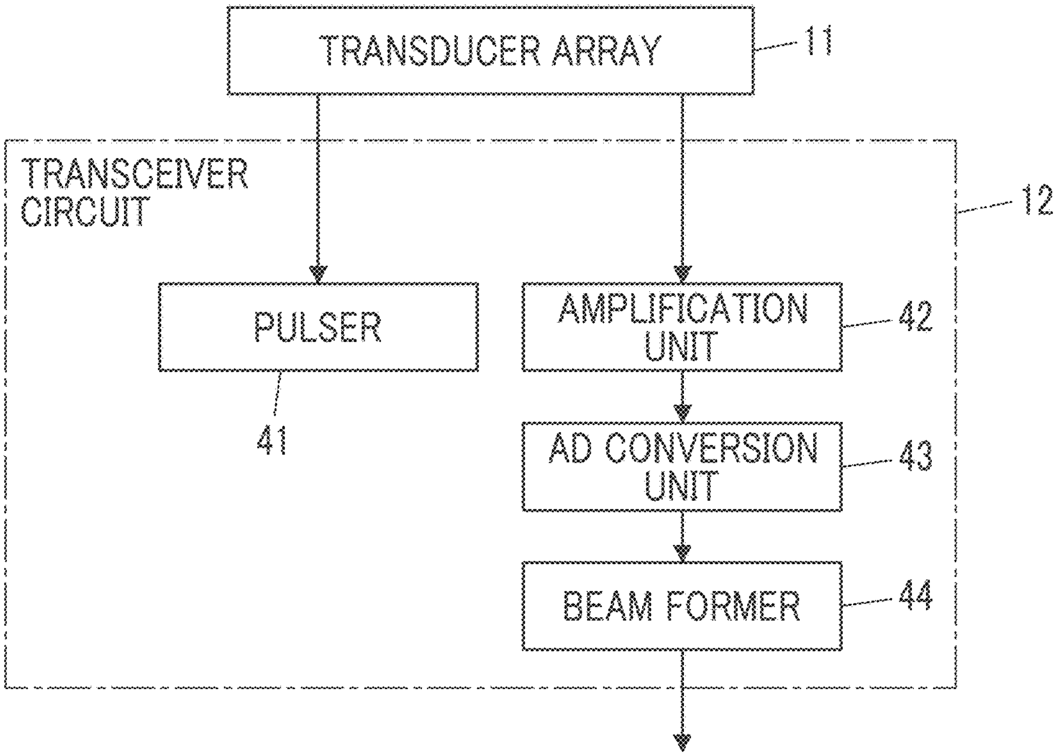
FIG. 2 is a block diagram showing a configuration of a transceiver circuit according to Embodiment 1 of the present invention.

Under the control of the body controller 29, the transceiver circuit 12 causes the transducer array 11 to transmit the ultrasound and generates a sound ray signal based on a reception signal acquired by the transducer array 11. As shown in FIG. 2, the transceiver circuit 12 includes a pulser 41 connected to the transducer array 11, and an amplifying unit 42, an analog-to-digital (AD) conversion unit 43, and a beam former 44 that are sequentially connected in series to the transducer array 11.

The pulser 41 includes, for example, a plurality of pulse generators, and the pulser 41 adjusts an amount of delay of each drive signal such that the ultrasound transmitted from the plurality of ultrasound transducers of the transducer array 11 form the ultrasound beam, based on a transmission delay pattern selected in accordance with a control signal from the body controller 29, and supplies the adjusted signal to the plurality of ultrasound transducers. In this way, in a case in which a pulsed or continuous wave-like voltage is applied to the electrodes of the ultrasound transducer of the transducer array 11, the piezoelectric material expands and contracts to generate pulsed or continuous wave-like ultrasound from each of the ultrasound transducers, whereby the ultrasound beam is formed from the combined wave of the ultrasound.

The transmitted ultrasound beam is, for example, reflected in a target such as a part of the subject and propagates toward the transducer array 11 of the ultrasound probe 1. The ultrasound echo propagating toward the transducer array 11 in this way is received by each of the ultrasound transducers constituting the transducer array 11. In this case, each of the ultrasound transducers constituting the transducer array 11 receives the propagating ultrasound echo to expand and contract to generate the reception signal, which is an electrical signal, and outputs these reception signals to the amplifying unit 42.

The amplifying unit 42 amplifies the signal input from each of the ultrasound transducers constituting the transducer array 11 and transmits the amplified signal to the AD conversion unit 43. The AD conversion unit 43 converts the signal transmitted from the amplifying unit 42 into digital reception data. The beam former 44 performs so-called reception focus processing by applying and adding the delay to each reception data received from the AD conversion unit 43. By this reception focus processing, each reception data converted by the AD conversion unit 43 is phase-added, and the sound ray signal in which the focus of the ultrasound echo is narrowed down is acquired.

Figure 3:
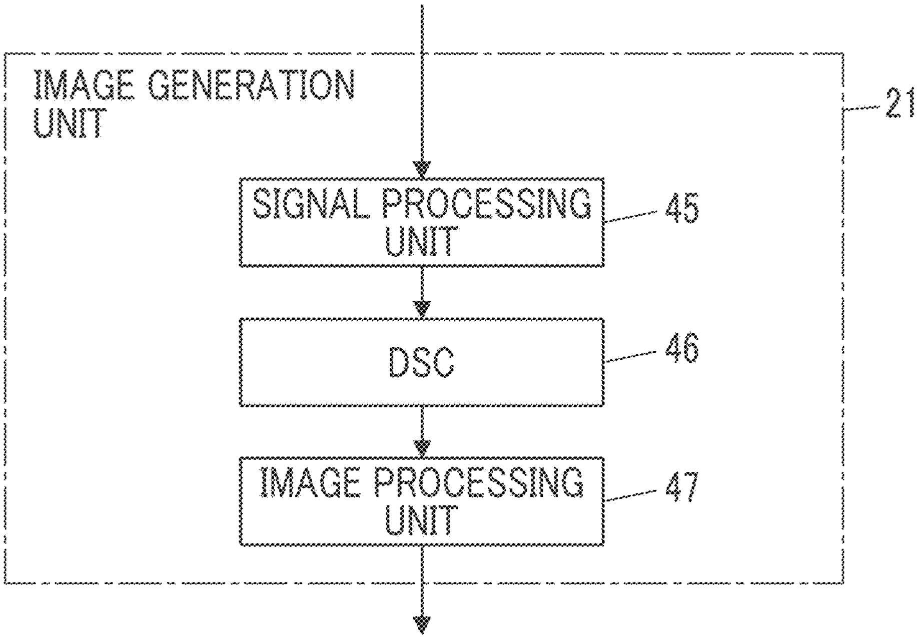
FIG. 3 is a block diagram showing a configuration of an image generation unit according to Embodiment 1 of the present invention.

As shown in FIG. 3, the image generation unit 21 has a configuration in which a signal processing unit 45, a digital scan converter (DSC) 46, and an image processing unit 47 are sequentially connected in series to each other.

The signal processing unit 45 generates a B-mode image signal, which is tomographic image information related to tissues inside the subject, by performing, on the sound ray signal received from the transceiver circuit 12, correction of the attenuation due to a distance in accordance with a depth of a reflection position of the ultrasound by using a sound velocity value set by the body controller 29 and then performing envelope detection processing.

The DSC 46 converts (raster-converts) the B-mode image signal generated by the signal processing unit 45 into the image signal in accordance with a normal television signal scanning method.

The image processing unit 47 performs various types of necessary image processing such as gradation processing on the B-mode image signal input from the DSC 46, and then transmits the B-mode image signal to the display controller 22 and the image memory 24. Hereinafter, the B-mode image signal that is image-processed by the image processing unit 47 will be referred to as an ultrasound image.

The probe tracking sensor 13 is a sensor device that acquires position/posture information of the ultrasound probe 1 under the control of the body controller 29. Here, in general, in a case in which the user performs an examination on the subject using the ultrasound diagnostic apparatus, the user often performs the examination while changing the posture of the ultrasound probe 1, that is, an inclination angle and a rotation angle of the ultrasound probe 1 in a state in which the ultrasound probe 1 is in contact with a body surface of the subject and moving the position of the ultrasound probe 1. The position/posture information of the ultrasound probe 1 acquired by the probe tracking sensor 13 includes information on the posture and the position of the ultrasound probe 1. The probe tracking sensor 13 can include, for example, at least one of a so-called inertial sensor, a magnetic sensor, an optical sensor, or an optical camera. The inertial sensor can include, for example, at least one of a so-called acceleration sensor or a gyro sensor.

The image memory 24 is a memory in which the ultrasound image generated by the image generation unit 21, the position/posture information of the ultrasound probe 1 acquired by the probe tracking sensor 13, and the three-dimensional ultrasound image acquired by the three-dimensional ultrasound image acquisition unit 31 are stored. Here, as the image memory 24, for example, a recording medium such as a flash memory, a hard disk drive (HDD), a solid-state drive (SSD), a flexible disk (FD), a magneto-optical disk (MO disk), a magnetic tape (MT), a random-access memory (RAM), a compact disc (CD), a digital versatile disc (DVD), a secure digital card (SD card), or a universal serial bus memory (USB memory) can be used.

Here, the ultrasound image generated by the image generation unit 21 and the position/posture information of the ultrasound probe 1 acquired by the probe tracking sensor 13 in a case in which the ultrasound image is generated are stored in the image memory 24 in association with each other.

The three-dimensional ultrasound image generation unit 25 generates the three-dimensional ultrasound image of the organ of the subject based on the ultrasound images of a plurality of frames generated by the image generation unit 21. The three-dimensional ultrasound image generation unit 25 can generate the three-dimensional ultrasound image of the organ, for example, by arranging the ultrasound images of the plurality of frames in accordance with the position/posture information of the corresponding ultrasound probe 1.

It should be noted that the three-dimensional ultrasound image generation unit 25 can sequentially perform processing of generating the three-dimensional ultrasound image each time the ultrasound image is generated by the image generation unit 21. In addition, the three-dimensional ultrasound image generation unit 25 can also perform processing of collectively generating a three-dimensional ultrasound image for the ultrasound images of a certain number of a plurality of frames stored in the image memory 24.

The template memory 26 is a memory in which a plurality of organ templates for a specific organ of the subject are stored. The plurality of organ templates represent a plurality of three-dimensional shapes of the organ deformed in accordance with a posture of the subject, such as a so-called sitting posture, decubitus posture, ventral decubitus posture, or lateral decubitus posture. That is, the template memory 26 stores, for the specific organ, the plurality of organ templates corresponding to the posture of the subject, such as an organ template corresponding to the sitting posture, an organ template corresponding to the decubitus posture, an organ template corresponding to the ventral decubitus posture, and an organ template corresponding to the lateral decubitus posture. It should be noted that, as the organ template corresponding to the lateral decubitus posture, both the organ templates of a left lateral decubitus posture in which the subject lies on a left side and a right lateral decubitus posture in which the subject lies on a right side can be used.

Figure 4:
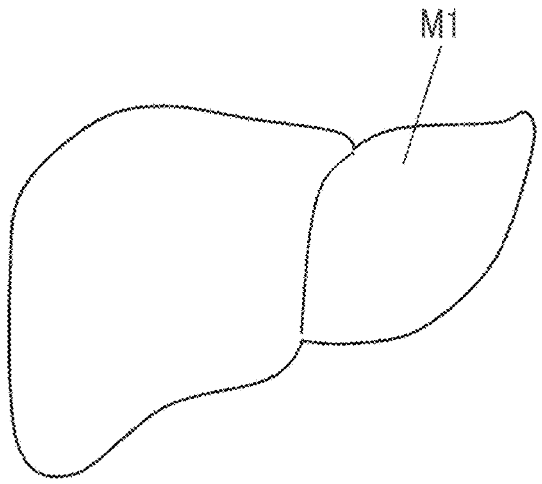
FIG. 4 is a diagram showing an example of an organ template corresponding to a liver.
Figure 5:
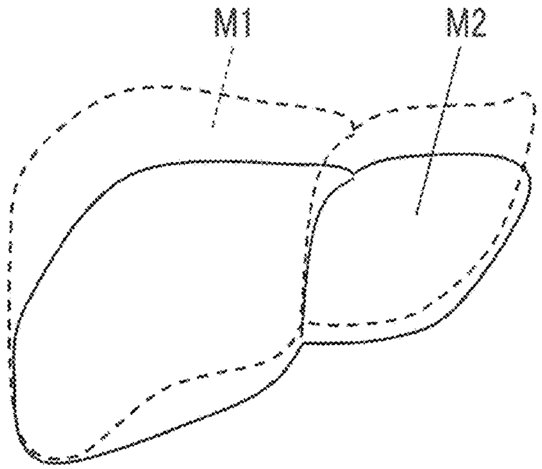
FIG. 5 is a diagram showing another example of the organ template corresponding to the liver.

For example, in a case in which the template memory 26 stores an organ template of a liver, the template memory 26 stores an organ template M1 representing a reference shape of the liver in the anatomy as shown in FIG. 4, as well as an organ template M2 representing a shape of the liver deformed from the reference shape by the application of an external force in accordance with a specific posture of the subject as shown in FIG. 5.

In addition, each of the plurality of organ templates stored in the template memory 26 may consist of three-dimensional data representing a contour of the organ in accordance with the posture of the subject, or may consist of three-dimensional data representing the contour of the organ and an internal structure of the organ in accordance with the posture of the subject.

As the template memory 26, for example, a recording medium such as a flash memory, an HDD, an SSD, an FD, an MO disk, an MT, a RAM, a CD, a DVD, an SD card, or a USB memory can be used.

The template selection unit 27 selects one organ template from among the plurality of organ templates stored in the template memory 26 in accordance with the posture of the subject. Here, the posture of the subject can be input by, for example, the user of the ultrasound diagnostic apparatus, such as a doctor, via the input device 30. For example, in a case in which the organ as an observation target is the liver and the sitting posture is input by the user as the posture of the subject, the template selection unit 27 can select the organ template of the liver corresponding to the sitting posture.

The scanning progress status output unit 28 specifies a scanning progress status of the ultrasound probe 1 for the organ as the observation target by performing registration between the three-dimensional ultrasound image acquired by the three-dimensional ultrasound image acquisition unit 31 and one organ template selected by the template selection unit 27, and outputs the specified scanning progress status.

The scanning progress status output unit 28 can perform the registration between the three-dimensional ultrasound image and one organ template by, for example, an algorithm such as a so-called random sample consensus (RANSAC) or an iterative closest point (ICP), a so-called machine learning method, or a combination thereof. It should be noted that the processing of the registration can include, for example, processing of deforming the three-dimensional ultrasound image or one organ template.

Figure 6:
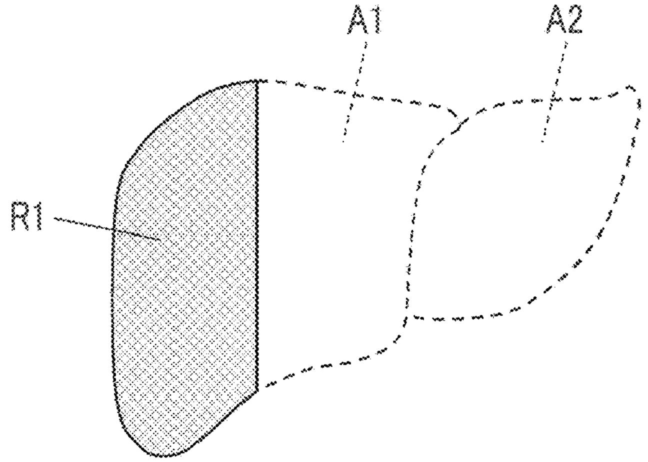
FIG. 6 is a diagram showing a display example of a region that has been scanned.

Here, the scanning progress status of the ultrasound probe 1 indicates a progress degree of the scanning using the ultrasound probe 1 for the organ as the observation target. The scanning progress status output unit 28 can specify a region that has been scanned using the ultrasound probe 1 in the organ as the observation target as the scanning progress status, to display the region that has been scanned, on the monitor 23. For example, in a case in which the organ as the observation target is the liver, the scanning progress status output unit 28 can display a region R1 that has been scanned, on the monitor 23 in a state of being superimposed on the organ template of the liver selected by the template selection unit 27 as shown in FIG. 6. This example shows that the scanning of a part of a right lobe A1 of the liver is completed out of the right lobe A1 and a left lobe A2.

Figure 7:
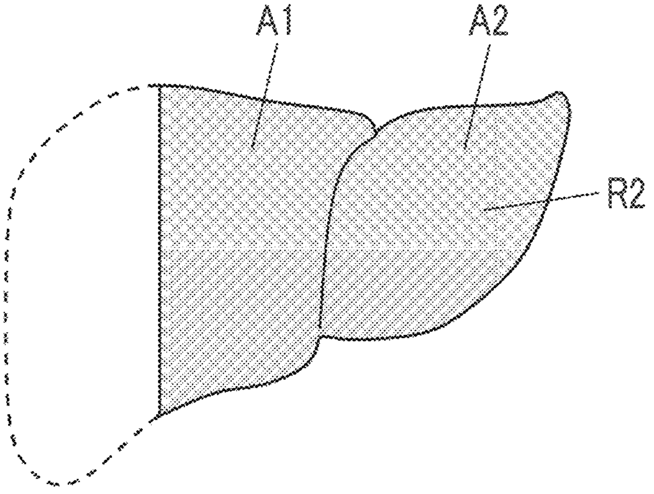
FIG. 7 is a diagram showing a display example of a region that has not yet been scanned.

In addition, the scanning progress status output unit 28 can specify a region of the organ as the observation target that has not yet been scanned using the ultrasound probe 1 as the scanning progress status, to display the region that has not yet been scanned, on the monitor 23. For example, in a case in which the organ as the observation target is the liver, the scanning progress status output unit 28 can display a region R2 that has not yet been scanned, on the monitor 23 in a state of being superimposed on the organ template of the liver selected by the template selection unit 27 as shown in FIG. 7. This example shows that the scanning of a part of the right lobe A1 and the entire left lobe A2 of the liver is not completed out of the right lobe A1 and the left lobe A2.

The display controller 22 performs predetermined processing on the ultrasound image transmitted from the image generation unit 21, the scanning progress status of the ultrasound probe 1 output by the scanning progress status output unit 28, and the like, and displays the ultrasound image, the scanning progress status, and the like on the monitor 23, under the control of the body controller 29.

The monitor 23 is a monitor for displaying the ultrasound image, the scanning progress status, and the like under the control of the display controller 22, and includes a display device such as a liquid crystal display (LCD), or an organic electroluminescence (EL) display.

The body controller 29 controls the respective units of the apparatus body 2, the transceiver circuit 12 of the ultrasound probe 1, and the probe tracking sensor 13 based on a control program and the like stored in advance.

The input device 30 is an input device for the user to perform an input operation, and is configured by, for example, a device such as a keyboard, a mouse, a trackball, a touchpad, and a touch sensor disposed in a state of being superimposed on the monitor 23.

It should be noted that the processor 32 including the image generation unit 21, the display controller 22, the three-dimensional ultrasound image generation unit 25, the template selection unit 27, the scanning progress status output unit 28, and the body controller 29 is configured by a central processing unit (CPU) and the control program for causing the CPU to execute various types of processing, but the processor 32 may be configured by a field programmable gate array (FPGA), a digital signal processor (DSP), an application specific integrated circuit (ASIC), a graphics processing unit (GPU), or other integrated circuits (IC), or may be configured by a combination thereof.

In addition, the image generation unit 21, the display controller 22, the three-dimensional ultrasound image generation unit 25, the template selection unit 27, the scanning progress status output unit 28, and the body controller 29 can also be configured by being integrated partially or entirely into one CPU or the like.

Next, an operation of the ultrasound diagnostic apparatus according to Embodiment 1 will be described with reference to the flowchart shown in FIG. 8. Hereinafter, a case will be described in which the organ as the observation target of the subject is the liver.

In step ST1, the posture of the subject is input by the user via the input device 30. In this case, the body controller 29 receives the posture of the subject input by the user.

In step ST2, the template selection unit 27 selects one organ template corresponding to the posture of the subject which is input by the user in step ST1 and received by the body controller 29, from among the plurality of organ templates of the liver stored in the template memory 26.

In step ST3, the image generation unit 21 generates the ultrasound image of the liver of the subject. In this case, under the control of the body controller 29, the transmission and reception of the ultrasound from the plurality of transducers of the transducer array 11 are started in accordance with the drive signal from the pulser 41 of the transceiver circuit 12 of the ultrasound probe 1, the ultrasound echo from the subject is received by the plurality of transducers of the transducer array 11, and the reception signal as the analog signal is output to the amplifying unit 42, is amplified, and then is subjected to the AD conversion via the AD conversion unit 43 to acquire the reception data.

The reception focus processing is performed on the reception data by the beam former 44, and the sound ray signal generated by the reception focusing processing is transmitted to the image generation unit 21 of the apparatus body 2, thereby the ultrasound image representing the tomographic image information of the subject is generated by the image generation unit 21. In this case, the signal processing unit 45 of the image generation unit 21 performs the correction of the attenuation in accordance with the depth of the reflection position of the ultrasound and the envelope detection processing on the sound ray signal, the DSC 46 performs the conversion into the image signal in accordance with the normal television signal scanning method, and the image processing unit 47 performs various types of necessary image processing such as gradation processing. The ultrasound image generated in step ST3 in this way is displayed on the monitor 23 via the display controller 22.

In a case in which the ultrasound image is generated in step ST3, the probe tracking sensor 13 acquires the position/posture information of the ultrasound probe 1. The ultrasound image generated in step ST3 and the acquired position/posture information of the ultrasound probe 1 are stored in the image memory 24 in association with each other.

In step ST4, the body controller 29 determines whether or not the ultrasound image is sufficiently acquired in the generation of the three-dimensional ultrasound image. The body controller 29 can determine whether or not the ultrasound image is sufficiently acquired, for example, by determining whether or not a predetermined time has elapsed since the start of step ST1. More specifically, for example, the body controller 29 can determine that the ultrasound image can be sufficiently acquired in a case in which the predetermined time has elapsed since the start of step ST1, and can determine that the ultrasound image cannot be sufficiently acquired in a case in which the predetermined time has not yet elapsed.

In addition, the body controller 29 can also determine whether or not the ultrasound image is sufficiently acquired by determining whether or not the movement of the ultrasound probe 1 is stopped after being moved by the user, for example, with reference to the position/posture information acquired in step ST3. More specifically, for example, the body controller 29 can determine that the ultrasound image can be sufficiently acquired in a case in which the movement of the ultrasound probe 1 is stopped after being moved by the user, and can determine that the ultrasound image cannot be sufficiently acquired in a case in which the ultrasound probe 1 continues to move.

In a case in which it is determined in step ST4 that the ultrasound image used for the generation of the three-dimensional ultrasound image is not sufficiently acquired, the processing returns to step ST3, the ultrasound image is newly generated, and the ultrasound image is stored in the image memory 24 along with the position/posture information of the ultrasound probe 1. In this way, the pieces of processing of steps ST3 and ST4 are repeated until it is determined in step ST4 that the ultrasound image is sufficiently acquired.

In a case in which it is determined in step ST4 that the ultrasound image to be used for the generation of the three-dimensional ultrasound image is sufficiently acquired, the processing proceeds to step ST5. In step ST5, the three-dimensional ultrasound image generation unit 25 generates the three-dimensional ultrasound image of the liver of the subject based on a plurality of pieces of the position/posture information of the ultrasound probe 1 and the ultrasound images of the plurality of frames obtained by repeating step ST3 and step ST4. In this case, for example, the three-dimensional ultrasound image generation unit 25 can generate the three-dimensional ultrasound image of the liver by arranging the ultrasound images of the plurality of frames in accordance with the position/posture information of the ultrasound probe 1 associated with each ultrasound image.

In step ST6, the scanning progress status output unit 28 specifies the scanning progress status of the ultrasound probe 1 with respect to the liver by performing the registration between one organ template selected in step ST2 and the three-dimensional ultrasound image of the liver acquired in step ST5 by using an algorithm such as RANSAC and ICP, a machine learning method, a combination thereof, or the like.

In this way, since the organ template representing the shape of the liver corresponding to the posture of the subject is used for the registration with the three-dimensional ultrasound image of the liver, even in a case in which the liver of the subject is deformed due to the posture of the subject, the three-dimensional ultrasound image can be accurately registered with the organ template. As a result, for example, the region R1 that has been scanned or the region R2 that has not yet been scanned in the liver can be accurately specified as the scanning progress status of the ultrasound probe 1.

In step ST7, the scanning progress status output unit 28 outputs the scanning progress status specified in step ST6. For example, as shown in FIG. 6 or 7, the scanning progress status output unit 28 can display the region R1 that has been scanned or the region R2 that has not yet been scanned in the liver on the monitor 23 as the scanning progress status of the ultrasound probe 1 in a state of being superimposed on one organ template selected in step ST2.

In step ST8, the body controller 29 determines whether or not to end the observation of the liver of the subject. The body controller 29 can determine to end the observation of the liver in a case in which the user determines that the liver of the subject can be comprehensively observed by, for example, checking the scanning progress status output in step ST7 and inputs an instruction to end the observation via the input device 30. The body controller 29 can determine to continue the observation of the liver in a case in which the user determines that the liver of the subject cannot be yet comprehensively observed by, for example, checking the scanning progress status output in step ST7 and does not input the instruction to end the observation.

The pieces of processing of step ST3 to step ST8 are repeated as long as it is determined to continue the observation of the liver in step ST8. In step ST3 in the repetition of steps ST3 to ST8, the three-dimensional ultrasound image generation unit 25 adds the data corresponding to the newly acquired ultrasound images of the plurality of frames to the already acquired three-dimensional ultrasound image of the liver, to generate the three-dimensional ultrasound image of the liver. Therefore, the scanning progress status of the ultrasound probe 1, which is specified in step ST6 and output in step ST7, is updated at any time by repeating step ST3 to step ST8. The user can continue the scanning while checking the scanning progress status of the ultrasound probe 1 which is updated at any time by repeating steps ST3 to ST8, and thus can easily and accurately perform the comprehensive observation of the liver of the subject regardless of the skill level of the user.

Figure 8:
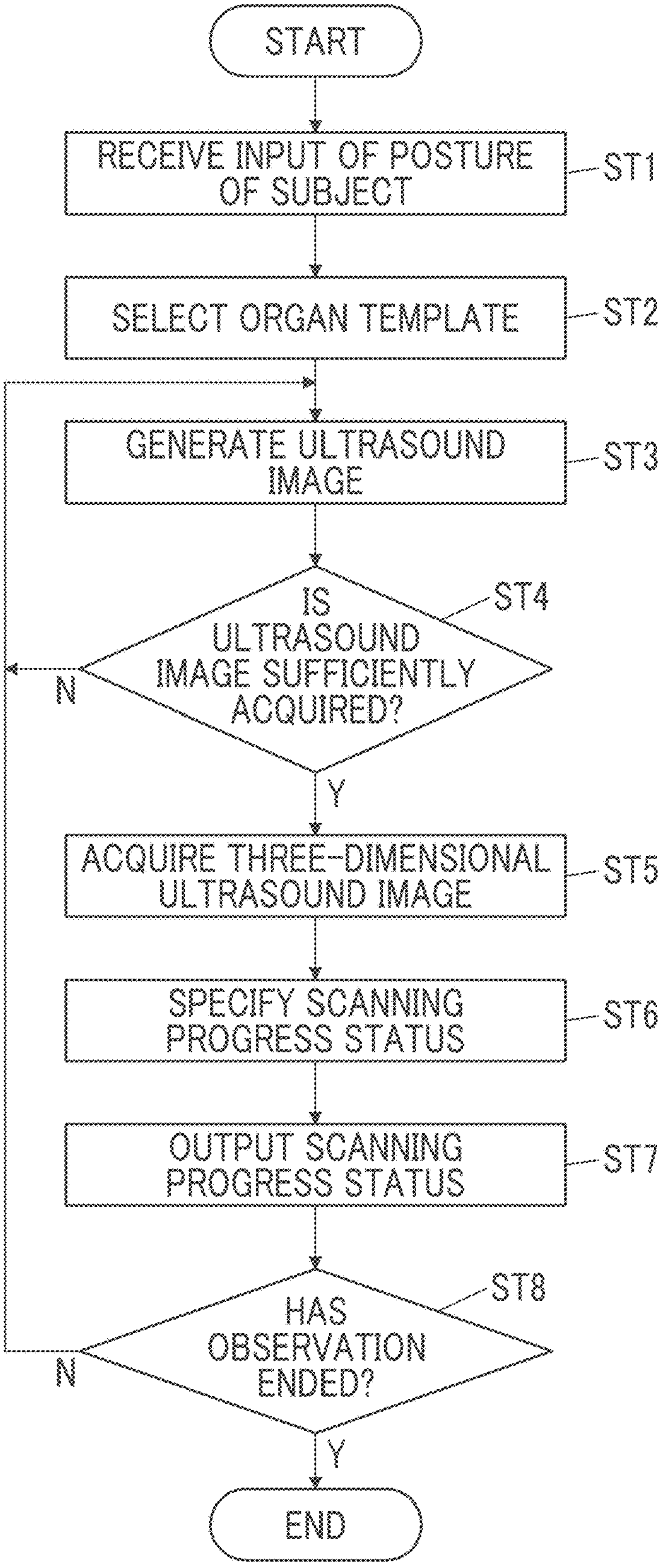
FIG. 8 is a flowchart showing an operation of the ultrasound diagnostic apparatus according to Embodiment 1 of the present invention.

In a case in which it is determined in step ST8 to end the observation of the liver, the operation of the ultrasound diagnostic apparatus according to the flowchart of FIG. 8 is completed.

As described above, with the ultrasound diagnostic apparatus according to Embodiment 1, the template memory 26 stores the plurality of organ templates for the organ as the observation target, the template selection unit 27 selects one organ template from among the plurality of organ templates in accordance with the posture of the subject, and the scanning progress status output unit 28 performs the registration between the acquired three-dimensional ultrasound image and the selected one organ template, specifies the scanning progress status of the ultrasound probe 1 for the organ as the observation target, and outputs the specified scanning progress status, so that it is possible for the user to easily and accurately perform the comprehensive observation of the organ as the observation target regardless of the skill level.

It should be noted that the description has been made in which the ultrasound probe 1 comprises the transceiver circuit 12, but the apparatus body 2 may comprise the transceiver circuit 12.

In addition, the description has been made in which the apparatus body 2 comprises the image generation unit 21, but the ultrasound probe 1 may comprise the image generation unit 21.

In addition, the apparatus body 2 may be a so-called stationary type, a portable type that is easy to carry, or a so-called hand-held type configured by, for example, a smartphone or tablet computer. As described above, the type of the device constituting the apparatus body 2 is not particularly limited.

In addition, the scanning progress status output unit 28 can output the scanning progress status for each section, for example, by dividing the organ as the observation target into a plurality of sections, quantifying the scanning progress status of the ultrasound probe 1 in each of the plurality of sections, and outputting the quantified scanning progress status. For example, the scanning progress status output unit 28 can divide the liver of the subject into two sections of the right lobe A1 and the left lobe A2, and output a ratio of the region R1 that has been scanned or a ratio of the region R2 that has not yet been scanned, in each section in, for example, a percentage such as "right lobe: ○○%, left lobe: ○○%".

Figure 9:
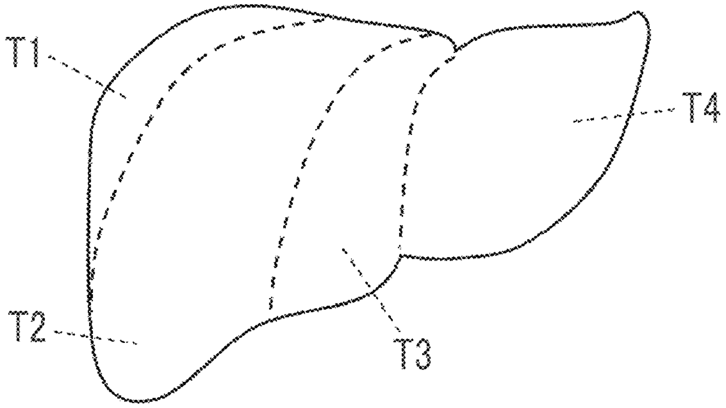
FIG. 9 is a diagram showing an example of a plurality of sections of the liver.
Figure 10:
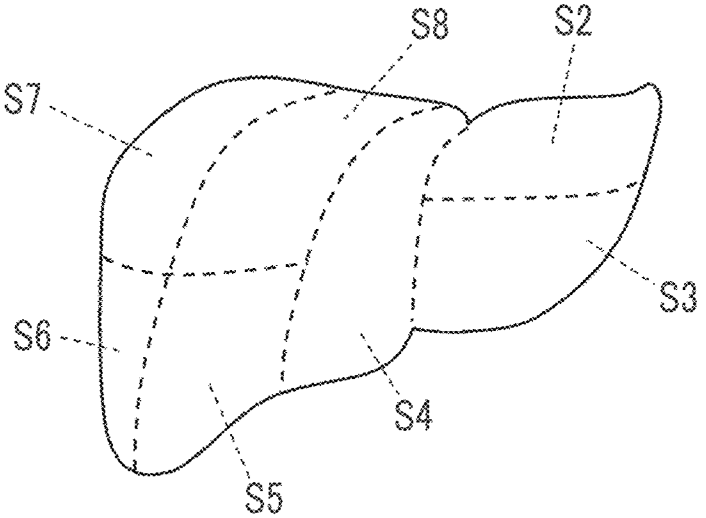
FIG. 10 is a diagram showing another example of the plurality of sections of the liver.

In addition, for example, the scanning progress status output unit 28 can also divide the liver into four sections of a rear section T1, an front section T2, an inner section T3, and an outer section T4 as shown in FIG. 9, or can also divide the liver into eight sub-sections S1 to S8 (sub-section S1 is not shown because the sub-section S1 is inside the liver) as shown in FIG. 10.

The scanning progress status output unit 28 can display the scanning progress status specified in this way for each of the plurality of sections on the monitor 23 as, for example, a numerical value. The scanning progress status output unit 28 can also display the scanning progress status specified for each of the plurality of sections on the monitor 23, for example, by displaying a so-called progress bar on the monitor 23. In addition, in a case in which the ultrasound diagnostic apparatus includes a speaker (not shown), the scanning progress status output unit 28 can also output the scanning progress status specified for each of the plurality of sections as a voice, for example, via the speaker.

In addition, the scanning progress status output unit 28 can output a section in which further scanning using the ultrasound probe 1 is recommended among the plurality of sections based on the quantified scanning progress statuses of the ultrasound probe 1 in the plurality of sections. The scanning progress status output unit 28 can output, for example, a section having the lowest ratio of the region R1 that has been scanned (section having the highest ratio of the region R2 that has not yet been scanned) among the plurality of sections of the organ as the observation target, as the section for which further scanning is recommended. The user can understand the section in which the scanning is not sufficiently performed by checking the output of the section for which the further scanning is recommended. The user can easily and reliably perform the comprehensive observation by performing the scanning using the ultrasound probe 1 comprehensively on the output sections while preferentially scanning the section in which the scanning is not sufficiently performed.

In addition, in general, it is known that, in a case in which a portion in which an object, such as a bone, through which it is difficult for the ultrasound to be transmitted is located is scanned using the ultrasound probe 1, a so-called acoustic shadow is generated by the bone or the like in the captured ultrasound image. For example, the three-dimensional ultrasound image generation unit 25 can detect a region representing the acoustic shadow in the generated three-dimensional ultrasound image, and the scanning progress status output unit 28 can exclude the region representing the acoustic shadow from the region R1 that has been scanned or output the region representing the acoustic shadow as the region R2 that has not yet been scanned. Here, the three-dimensional ultrasound image generation unit 25 can detect the region representing the acoustic shadow in the three-dimensional ultrasound image by using, for example, a trained model in machine learning, which has learned a large number of ultrasound images including the acoustic shadow.

In this way, by excluding the region representing the acoustic shadow from the region R1 that has been scanned or outputting the region representing the acoustic shadow as the region R2 that has not yet been scanned, the scanning progress status of the ultrasound probe 1 can be more accurately output, and thus the user can more reliably perform the comprehensive observation of the organ as the observation target.

In addition, in general, it is known that, in a state of so-called aerial radiation, that is, in a state in which the ultrasound probe 1 is separated from the body surface of the subject and the ultrasound are radiated from the ultrasound probe 1 into the air, for example, an aerial radiation image, which is an ultrasound image in which the entire image is filled with a specific color such as black, is obtained. The body controller 29 can determine whether or not the aerial radiation image is generated by determining, for example, whether or not the entire ultrasound image generated by the image generation unit 21 is filled with the specific color such as black, and can determine that the observation of the organ as the observation target is stopped in a case in which it is determined that the aerial radiation image is generated. In this case, the body controller 29 can stop, for example, the processing of the three-dimensional ultrasound image generation unit 25.

As a result, it is possible to prevent the aerial radiation image from being added in a case of generating the three-dimensional ultrasound image, and the scanning progress status output unit 28 can more accurately output the scanning progress status of the ultrasound probe 1, so that the user can more reliably perform the comprehensive observation of the organ as the observation target.

In addition, a landmark, which is a portion having significant shape characteristics, may be present in the organ of the subject. For example, a branch point of a portal vein or an inferior vena cava is described as the landmark of the liver. In a case in which the three-dimensional ultrasound image of the landmark in the organ as the observation target can be accurately acquired, the three-dimensional ultrasound image of the organ as the observation target deformed by the posture of the subject can be more accurately acquired.

Therefore, the body controller 29 can issue an instruction to the user by, for example, displaying on the monitor 23 that pre-scanning for drawing the landmark, which is a portion that is likely to be greatly deformed in accordance with the posture of the subject, in the organ is performed before the user performs main scanning of the organ as the observation target, that is, the comprehensive observation of the entire organ as the observation target. In this case, the three-dimensional ultrasound image generation unit 25 can generate the three-dimensional ultrasound image of the landmark of the organ as the observation target. The body controller 29 determines whether or not a structure of the generated three-dimensional ultrasound image of the landmark is defective, for example, whether or not the shape of the three-dimensional ultrasound image of the portal vein, which is the landmark, is smoothly continuous, and can end the pre-scanning and start the main scanning in a case in which it is determined that the structure of the three-dimensional ultrasound image of the landmark is not defective.

Although it has been described that the three-dimensional ultrasound image generation unit 25 generates the three-dimensional ultrasound image based on the position/posture information of the ultrasound probe 1 acquired by the probe tracking sensor 13 and the ultrasound images of the plurality of frames generated by the image generation unit 21, the method of generating the three-dimensional ultrasound image is not particularly limited to this.

For example, in a case in which the ultrasound images of the plurality of frames are generated while the ultrasound probe 1 is moved in parallel in a certain direction or while the ultrasound probe 1 is inclined in a certain angle range while the ultrasound probe 1 is disposed at a fixed position, the three-dimensional ultrasound image generation unit 25 can generate the three-dimensional ultrasound image by arranging the ultrasound images of the plurality of frames generated by the image generation unit 21 in time series without using the position/posture information of the ultrasound probe 1 acquired by the probe tracking sensor 13.

In addition, in a case in which the transducer array 11 includes the plurality of ultrasound transducers arranged in a two-dimensional manner, the transceiver circuit 12 can acquire the ultrasound images of the plurality of frames by performing so-called electronic scanning. In this case, the three-dimensional ultrasound image generation unit 25 can generate the three-dimensional ultrasound image from the acquired ultrasound images of a plurality of frames based on a positional relationship of a plurality of tomographic planes scanned by electronic scanning.

Embodiment 2

In Embodiment 1, the description has been made in which the user inputs the posture of the subject via the input device 30, but the ultrasound diagnostic apparatus can also automatically detect the posture of the subject.

Figure 11:
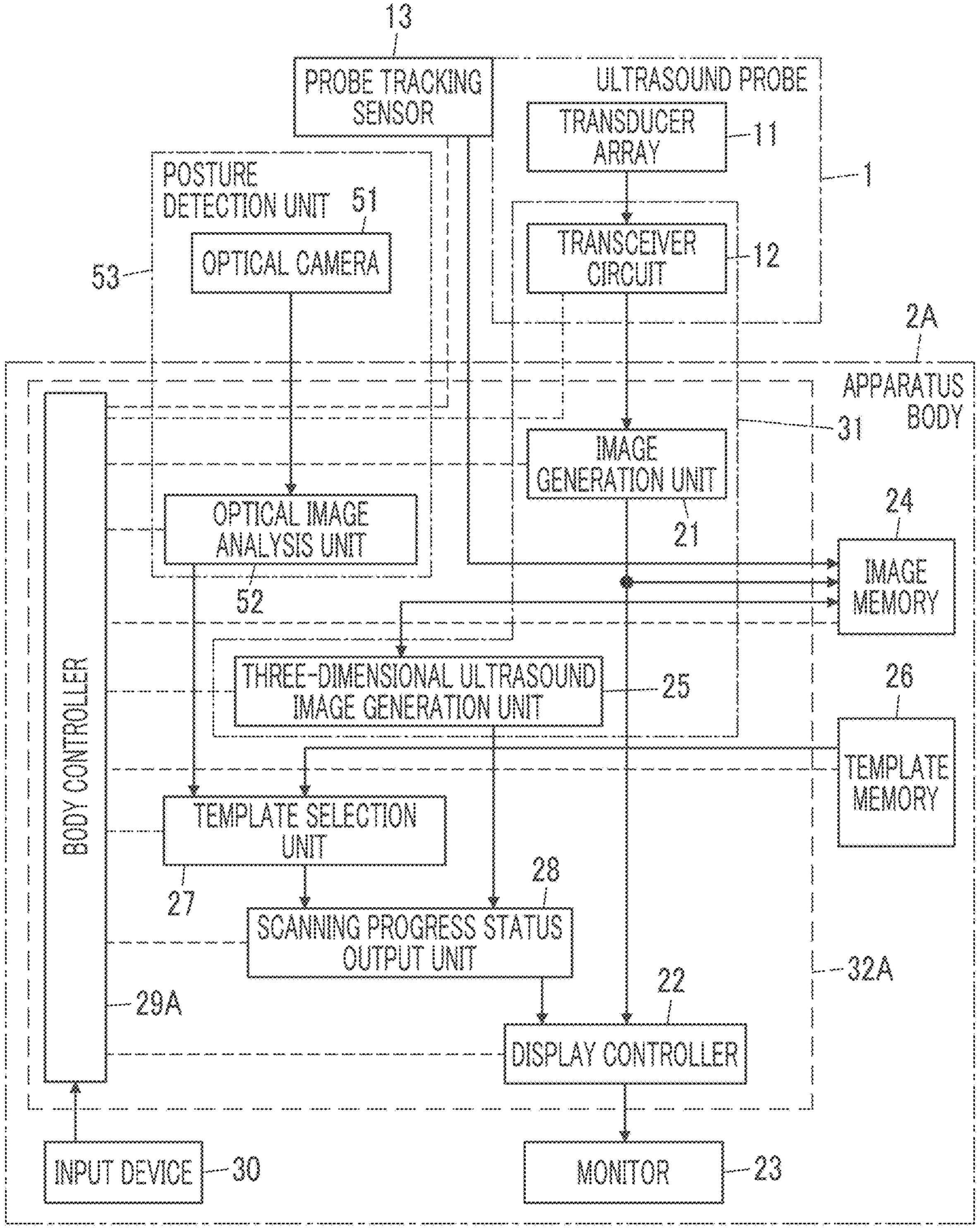
FIG. 11 is a block diagram showing a configuration of an ultrasound diagnostic apparatus according to Embodiment 2 of the present invention.

FIG. 11 shows a configuration of an ultrasound diagnostic apparatus according to Embodiment 2. The ultrasound diagnostic apparatus according to Embodiment 2 comprises an apparatus body 2A instead of the apparatus body 2 and further comprises an optical camera 51, with respect to the ultrasound diagnostic apparatus according to Embodiment 1 shown in FIG. 1. Although the optical camera 51 is provided outside the ultrasound probe 1 and the apparatus body 2A, for example, the optical camera 51 may be attached to or incorporated in the apparatus body 2A.

The apparatus body 2A comprises a body controller 29A instead of the body controller 29 and further comprises an optical image analysis unit 52, in the apparatus body 2 according to Embodiment 1. Here, the optical image analysis unit 52 is connected to the optical camera 51. The optical image analysis unit 52 is connected to the template selection unit 27 and the body controller 29A. The optical camera 51 and the optical image analysis unit 52 constitute a posture detection unit 53. In addition, in the apparatus body 2A, the image generation unit 21, the display controller 22, the three-dimensional ultrasound image generation unit 25, the template selection unit 27, the scanning progress status output unit 28, the body controller 29A, and the optical image analysis unit 52 constitute a processor 32A for the apparatus body 2A.

The optical camera 51 includes, for example, an image sensor such as a so-called charge-coupled device (CCD) image sensor or a so-called a complementary metal-oxide-semiconductor (CMOS) image sensor, and images the subject to acquire an optical image. The optical camera 51 transmits the acquired optical image to the optical image analysis unit 52.

The optical image analysis unit 52 analyzes the optical image acquired by the optical camera 51, to detect the posture of the subject. The optical image analysis unit 52 can detect the posture of the subject from the optical image, for example, by a method of using a trained model in machine learning, which has learned a relationship between the optical image in which the subject is shown and the posture of the subject.

The template selection unit 27 selects one organ template corresponding to the posture of the subject detected by the optical image analysis unit 52 from among the plurality of organ templates stored in the template memory 26 for the organ as the observation target.

The template selection unit 27 can calculate a degree of similarity with respect to the posture of the subject detected by the posture detection unit 53 for each of the plurality of organ templates stored in the template memory 26, for example, and select one organ template having the highest degree of similarity. In this case, the template selection unit 27 can calculate the degree of similarity by using, for example, an algorithm such as a so-called support-vector machine (SVM), a decision tree, deep learning, or collaborative filtering, or a combination of these algorithms.

In addition, the template selection unit 27 can also select one organ template by using, for example, a trained model in machine learning, which has learned a relationship between a detection result, which is the output from the posture detection unit 53 in accordance with the posture of the subject, and the organ template.

The scanning progress status output unit 28 specifies the scanning progress status of the ultrasound probe 1 by performing registration between the three-dimensional ultrasound image generated by the three-dimensional ultrasound image generation unit 25 and one organ template selected by the template selection unit 27, and outputs the specified scanning progress status.

As described above, with the ultrasound diagnostic apparatus according to Embodiment 2, the posture detection unit 53 configured by the optical camera 51 and the optical image analysis unit 52 automatically detects the posture of the subject from the optical image of the subject, so that the user does not need to input the posture of the subject via the input device 30, and can more easily perform the comprehensive observation of the organ of the subject.

It should be noted that the optical image of the subject captured by the optical camera 51 may be an image in which the entire body of the subject is imaged, or an image in which the subject is partially imaged, for example, only the upper body of the subject is imaged. The optical image analysis unit 52 can detect the posture of the subject based on the optical image obtained by imaging the entire body of the subject or the optical image obtained by partially imaging the subject by using, for example, a trained model in machine learning, which has learned a relationship between the optical image of the subject and the posture of the subject.

In addition, for example, in a case in which the degree of similarity of the posture of the subject is used for the selection of the organ template, a plurality of calculated degrees of similarity are very close to each other, and a difference thereof is within a certain value, the template selection unit 27 can also display the plurality of organ templates that may be used by the scanning progress status output unit 28, on the monitor 23. In this case, the template selection unit 27 can select, for example, one organ template designated by the user via the input device 30 from among the plurality of organ templates displayed on the monitor 23. In addition, the template selection unit 27 can select one organ template designated by the user in the same manner, for example, even in a case in which a trained model in machine learning is used for selecting the organ template and the trained model outputs the plurality of organ templates.

In addition, instead of the optical image of the subject acquired by the optical camera 51, for example, a signal related to the position of the body of the subject can be acquired by a sensor device such as an optical sensor, an infrared camera, an infrared sensor, a magnetic sensor, or light detection and ranging (LiDAR) (which are not shown), and the posture of the subject can be detected by analyzing the signal. In this case, a signal analysis unit (not shown) that analyzes the signal related to the position of the body of the subject can detect the posture of the subject from the signal related to the position of the body of the subject by using, for example, a method of comparing the acquired signal with a template of a signal indicating a plurality of postures of the subject, or a method of using a trained model in machine learning, which has learned a relationship between the signal and the posture of the subject.

Embodiment 3

The ultrasound diagnostic apparatus can also detect the posture of the subject based on a signal from a pressure sensor disposed on an examination table on which the subject is placed in a case in which the subject undergoes the examination. Here, the examination table according to the embodiment of the present invention includes a chair, a bed, and the like on which the subject is placed during the examination.

Figure 12:
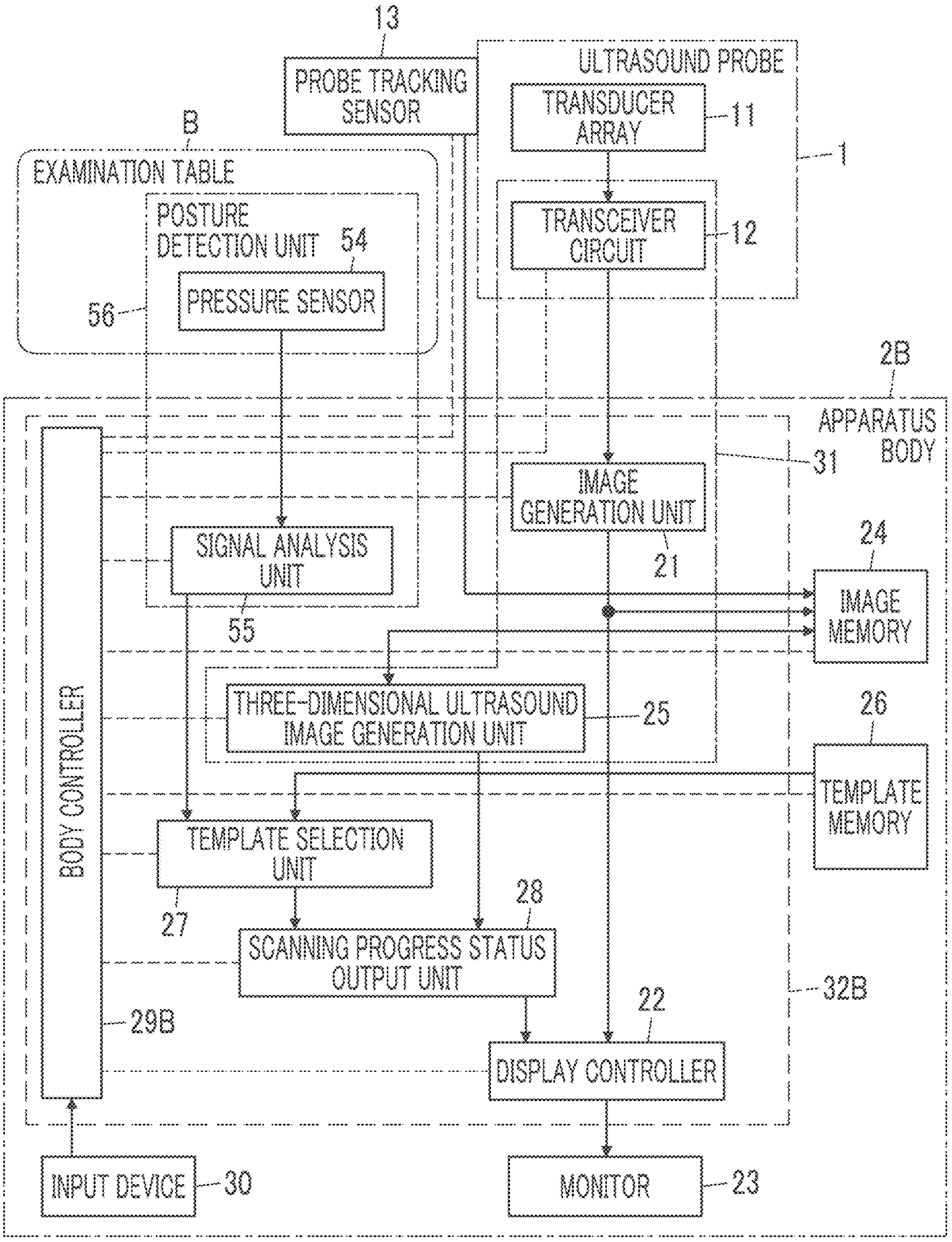
FIG. 12 is a block diagram showing a configuration of an ultrasound diagnostic apparatus according to Embodiment 3 of the present invention.

FIG. 12 shows a configuration of an ultrasound diagnostic apparatus according to Embodiment 3. The ultrasound diagnostic apparatus according to Embodiment 3 comprises an apparatus body 2B instead of the apparatus body 2A and comprises a plurality of pressure sensors 54 disposed on an examination table B instead of the optical camera 51 in the ultrasound diagnostic apparatus of Embodiment 2 shown in FIG. 11. The apparatus body 2B comprises a body controller 29B instead of the body controller 29A and comprises a signal analysis unit 55 instead of the optical image analysis unit 52 in the apparatus body 2A according to Embodiment 2.

The signal analysis unit 55 is connected to the plurality of pressure sensors 54 disposed on the examination table B. The signal analysis unit 55 is connected to the template selection unit 27 and the body controller 29B. The plurality of pressure sensors 54 and the signal analysis unit 55 constitute a posture detection unit 56. In addition, in the apparatus body 2B, the image generation unit 21, the display controller 22, the three-dimensional ultrasound image generation unit 25, the template selection unit 27, the scanning progress status output unit 28, the body controller 29B, and the signal analysis unit 55 constitute a processor 32B for the apparatus body 2B.

The plurality of pressure sensors 54 are disposed on the examination table B on which the subject is placed in a case in which the subject undergoes the examination, and detect a detection signal representing a distribution of pressure from the subject, which correspond to the posture of the subject. Since a shape and an area of a region in which the subject touches the bed vary depending on the posture of the subject on the bed, the detection signal representing the distribution of pressure corresponding to each posture of the subject is detected by the plurality of pressure sensors 54.

The signal analysis unit 55 analyzes the detection signals acquired by the plurality of pressure sensors 54, to detect the posture of the subject. The signal analysis unit 55 can store, for example, templates of a plurality of detection signals corresponding to a plurality of postures of the subject in advance, to detect the posture of the subject by comparing the detection signals acquired by the plurality of pressure sensors 54 with the templates. In addition, the signal analysis unit 55 can also detect the posture of the subject by using a trained model in machine learning, which has learned a relationship between the posture of the subject and the detection signal.

The template selection unit 27 selects one organ template corresponding to the posture of the subject detected by the signal analysis unit 55 from among the plurality of organ templates stored in the template memory 26 for the organ as the observation target.

The template selection unit 27 can calculate a degree of similarity with respect to the posture of the subject detected by the posture detection unit 56 for each of the plurality of organ templates stored in the template memory 26, for example, and select one organ template having the highest degree of similarity. In this case, the template selection unit 27 can calculate the degree of similarity by using, for example, an algorithm such as a so-called SVM, a decision tree, deep learning, or collaborative filtering, or a combination of these algorithms.

In addition, the template selection unit 27 can also select one organ template by using, for example, a trained model in machine learning, which has learned a relationship between a detection result, which is the output from the posture detection unit 56 in accordance with the posture of the subject, and the organ template.

The scanning progress status output unit 28 specifies the scanning progress status of the ultrasound probe 1 by performing registration between the three-dimensional ultrasound image generated by the three-dimensional ultrasound image generation unit 25 and one organ template selected by the template selection unit 27, and outputs the specified scanning progress status.

As described above, with the ultrasound diagnostic apparatus according to Embodiment 3, the posture detection unit 56 configured by the plurality of pressure sensors 54 and the signal analysis unit 55 automatically detects the posture of the subject from the detection signal of the pressure, so that the user does not need to input the posture of the subject via the input device 30, and can more easily perform the comprehensive observation of the organ of the subject, as in the ultrasound diagnostic apparatus according to Embodiment 2.

It should be noted that, although it has been described that the plurality of pressure sensors 54 are disposed on the examination table B, for example, in a case in which the examination table B is the chair, one pressure sensor 54 can be disposed on the chair. Since the posture of the subject placed on the chair is usually the sitting posture, the signal analysis unit 55 can detect the posture of the subject as the sitting posture in a case in which the detection signal of the pressure is received from the pressure sensor 54. In this way, the ultrasound diagnostic apparatus can comprise at least one pressure sensor 54 disposed on the chair or the examination table B.

For example, in a case in which there are a plurality of examination tables B in an examination room for examining the subject, the pressure sensor 54 can be disposed on each examination table B.

Embodiment 4

Although, in Embodiments 1 to 3, the template selection unit 27 selects one organ template for the organ as the observation target based on the information indicating the posture of the subject, for example, one organ template can also be selected based on the three-dimensional ultrasound image of the organ as the observation target.

Figure 13:
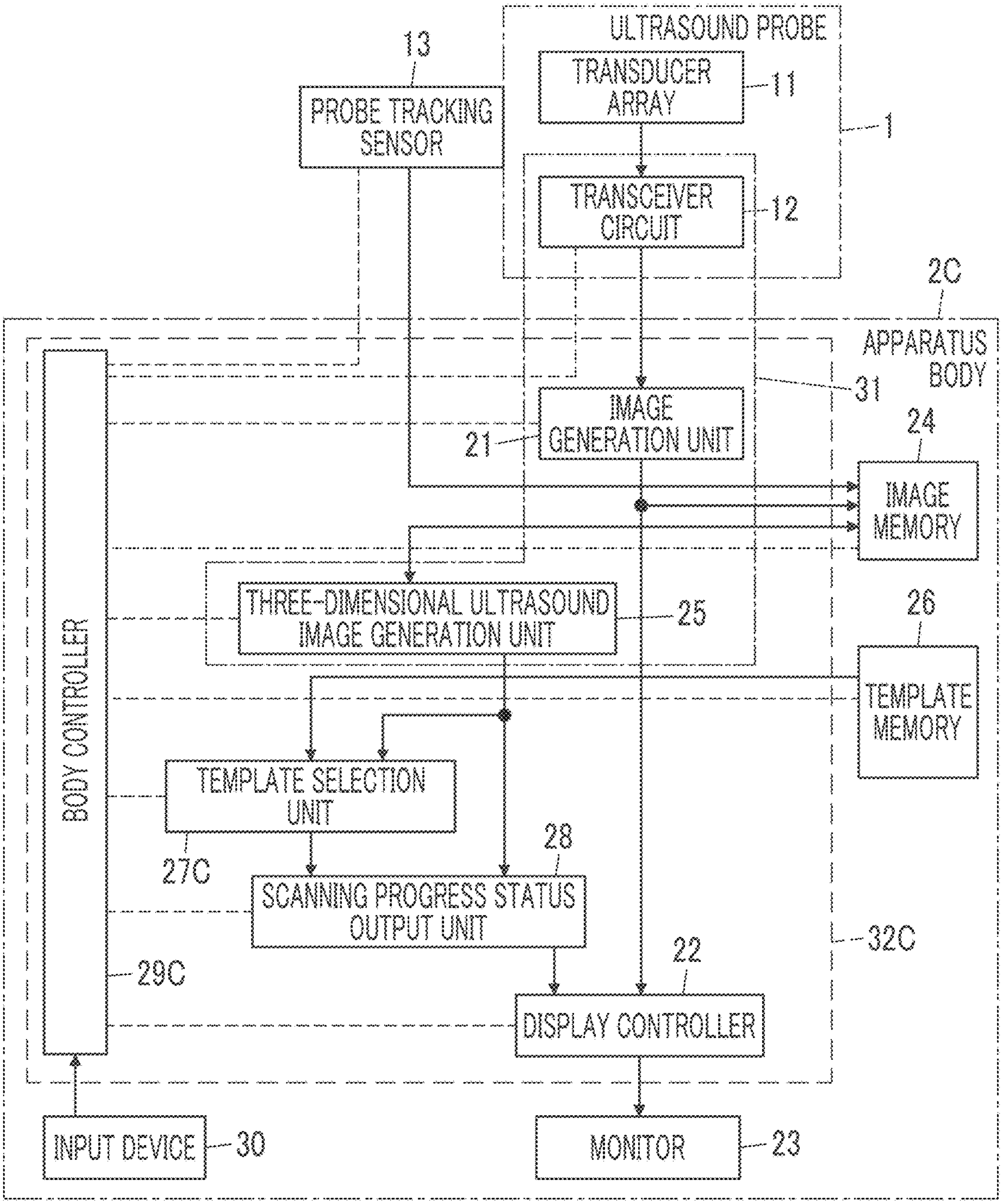
FIG. 13 is a block diagram showing a configuration of an ultrasound diagnostic apparatus according to Embodiment 4 of the present invention.

FIG. 13 shows a configuration of an ultrasound diagnostic apparatus according to Embodiment 4. The ultrasound diagnostic apparatus according to Embodiment 4 comprises an apparatus body 2C instead of the apparatus body 2 in the ultrasound diagnostic apparatus according to Embodiment 1 shown in FIG. 1. The apparatus body 2C comprises a template selection unit 27C instead of the template selection unit 27 and comprises a body controller 29C instead of the body controller 29 in the apparatus body 2 according to Embodiment 1.

In the apparatus body 2C, a template selection unit 27C is connected to the three-dimensional ultrasound image generation unit 25 and the template memory 26. The template selection unit 27C is connected to the scanning progress status output unit 28 and the body controller 29C. In addition, the image generation unit 21, the display controller 22, the three-dimensional ultrasound image generation unit 25, the template selection unit 27C, the scanning progress status output unit 28, and the body controller 29C constitute a processor 32C for the apparatus body 2C.

The template selection unit 27C selects one organ template based on the three-dimensional ultrasound image of the organ as the observation target acquired by the three-dimensional ultrasound image acquisition unit 31. For example, the template selection unit 27C can calculate a degree of similarity with respect to the three-dimensional ultrasound image acquired by the three-dimensional ultrasound image acquisition unit 31 for each of the plurality of organ templates stored in the template memory 26 for the organ as the observation target, and can select one organ template having the highest degree of similarity. In this case, the template selection unit 27C can calculate the degree of similarity by using, for example, an algorithm such as an SVM, a decision tree, deep learning, or collaborative filtering, or a combination of these algorithms.

In addition, the template selection unit 27C can also select one organ template by using, for example, a trained model in machine learning, which has learned the three-dimensional ultrasound image of the organ as the observation target in accordance with the posture of the subject.

The scanning progress status output unit 28 specifies the scanning progress status of the ultrasound probe 1 by performing registration between one organ template selected by the template selection unit 27C and the three-dimensional ultrasound image generated by the three-dimensional ultrasound image generation unit 25, and outputs the specified scanning progress status.

Figure 14:
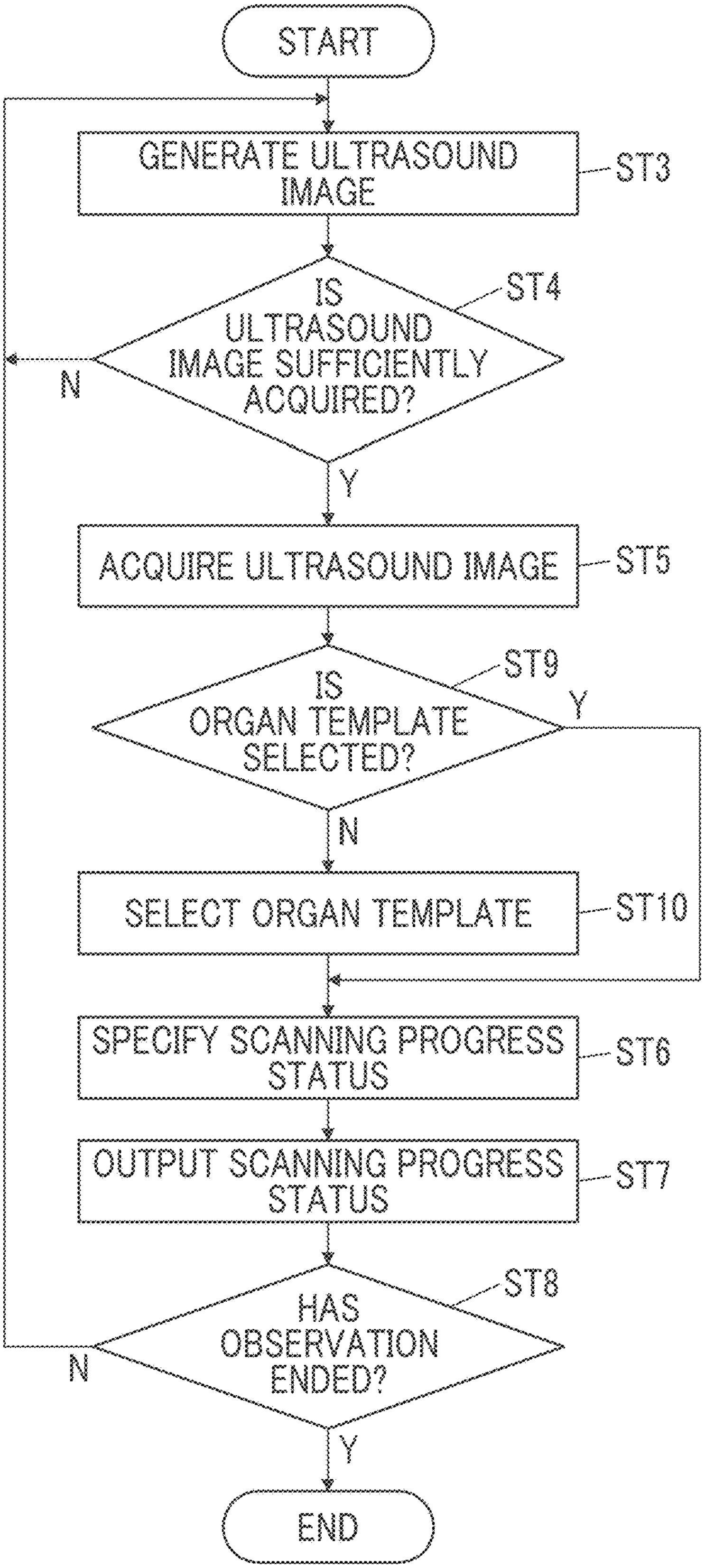
FIG. 14 is a flowchart showing an operation of the ultrasound diagnostic apparatus according to Embodiment 4 of the present invention.

Next, an example of an operation of the ultrasound diagnostic apparatus according to Embodiment 4 will be described with reference to the flowchart of FIG. 14. Steps ST3 to ST8 in the flowchart of FIG. 14 are the same as steps ST3 to ST8 in FIG. 8, and thus detailed description of these steps will be omitted. In addition, an example will be described in which the organ as the observation target is the liver.

First, in step ST3, the image generation unit 21 generates the ultrasound image of the liver of the subject. In this case, the probe tracking sensor 13 also acquires the position/posture information of the ultrasound probe 1, and the ultrasound image and the position/posture information of the ultrasound probe 1 corresponding to each other are stored in the image memory 24 in association with each other.

In step ST4, the body controller 29C determines whether or not the ultrasound image for generating the three-dimensional ultrasound image is sufficiently acquired. Here, the pieces of processing of steps ST3 and of ST4 are repeated until it is determined that the ultrasound image is sufficiently acquired. In a case in which it is determined in step ST4 that the ultrasound image for generating the three-dimensional ultrasound image is sufficiently acquired, the processing proceeds to step ST4.

In step ST5, the three-dimensional ultrasound image generation unit 25 generates the three-dimensional ultrasound image of the liver based on the ultrasound images of the plurality of frames obtained by repeating steps ST3 and ST4 and stored in the image memory 24.

In step ST9 following step ST5, the body controller 29C determines whether or not one organ template for the liver as the observation target is already selected. At this point in time, since one organ template is not yet selected, the body controller 29C determines that one organ template is not selected. In this case, the processing proceeds to step ST10.

In step ST10, the template selection unit 27C calculates the degree of similarity of each of the plurality of organ templates with respect to the liver stored in the image memory 24 to the three-dimensional ultrasound image of the liver acquired in step ST5, and selects one organ template having the highest degree of similarity. In this case, the template selection unit 27C can calculate the degree of similarity by using, for example, an algorithm such as an SVM, a decision tree, deep learning, or collaborative filtering, or a combination of these algorithms.

In addition, the template selection unit 27C can also select one organ template by using, for example, a trained model in machine learning, which has learned the three-dimensional ultrasound image of the organ as the observation target in accordance with the posture of the subject.

In step ST6 following step ST10, the scanning progress status output unit 28 specifies the scanning progress status of the ultrasound probe 1 with respect to the liver by performing registration between the three-dimensional ultrasound image of the liver acquired in step ST4 and one organ template selected in step ST9 by using an algorithm such as RANSAC and ICP, a machine learning method, a combination thereof, or the like.

In step ST7, the scanning progress status output unit 28 outputs the scanning progress status specified in step ST6.

In step ST8, the body controller 29C determines whether or not to end the observation of the liver of the subject. In a case in which it is determined to continue the observation of the liver in step ST8, the processing returns to step ST3. The ultrasound image of the liver of the subject is generated in step ST3, and it is determined in step ST4 whether or not the ultrasound image for generating the three-dimensional ultrasound image is sufficiently acquired.

In a case in which it is determined that the ultrasound image is sufficiently acquired, the processing proceeds to step ST5.

In step ST5, the three-dimensional ultrasound image generation unit 25 generates the three-dimensional ultrasound image of the liver by adding the data corresponding to the ultrasound images of the plurality of frames obtained by repeating steps ST3 and ST4 newly performed on the three-dimensional ultrasound image obtained in previous step ST5. In a case in which step ST5 is completed, the processing proceeds to step ST9.

In step ST9, the body controller 29C determines whether or not one organ template for the liver as the observation target is already selected. Since one organ template for the liver is already selected in the previous step ST10, the body controller 29C determines that one organ template is already selected. In this case, step ST10 is skipped, and the processing proceeds to step ST6.

In step ST6, the scanning progress status output unit 28 newly specifies the scanning progress status of the ultrasound probe 1 for the liver by performing registration between the three-dimensional ultrasound image of the liver newly acquired in step ST5 and one organ template already selected in previous step ST10. The scanning progress status specified in this way is output by the scanning progress status output unit 28 in step ST7.

In following step ST8, the body controller 29C determines whether or not to end the observation of the liver of the subject. The pieces of processing of steps ST3 to ST5, ST9, ST10, and ST6 to ST8 are repeated as long as it is determined to continue the observation of the liver in step ST8. In a case in which it is determined in step ST8 to end the observation of the liver, the operation of the ultrasound diagnostic apparatus in accordance with the flowchart of FIG. 14 is completed.

As described above, even in a case in which one organ template is selected based on the three-dimensional ultrasound image of the organ as the observation target and the plurality of organ templates stored in the template memory 26 for the organ as the observation target, the user can easily and accurately perform the comprehensive observation of the organ as the observation target regardless of the skill level of the user, as in a case in which one organ template is selected based on the information indicating the posture of the subject as in Embodiments 1 to 3.

It should be noted that, in the flowchart of FIG. 14, one organ template selected in step ST10 is continuously used in the following processing, but one organ template can be re-selected by performing the processing of step ST10 each time a new three-dimensional ultrasound image is acquired. By regularly updating one organ template used for registration in this way, even in a case in which the optimal organ template is not selected due to insufficient scanning of the organ as the observation target using the ultrasound probe 1 or the like, the optimal organ template can be selected by updating one organ template in the next and subsequent times, and the accurate scanning progress status can be output.

In addition, for example, in a case in which the degree of similarity between the organ template and the three-dimensional ultrasound image is used for the selection of the organ template, the plurality of calculated degrees of similarity are very close to each other, and the difference thereof is within a certain value, the template selection unit 27 can also display the plurality of organ templates that may be used by the scanning progress status output unit 28, on the monitor 23. In this case, the template selection unit 27 can select, for example, one organ template designated by the user via the input device 30 from among the plurality of organ templates displayed on the monitor 23. In addition, the template selection unit 27 can select one organ template designated by the user in the same manner, for example, even in a case in which a trained model in machine learning is used for selecting the organ template and the trained model outputs the plurality of organ templates.

EXPLANATION OF REFERENCES

1: ultrasound probe
2, 2A, 2B, 2C: apparatus body
11: transducer array
12: transceiver circuit
13: probe tracking sensor
21: image generation unit
22: display controller
23: monitor
24: image memory
25: three-dimensional ultrasound image generation unit
26: template memory
27, 27C: template selection unit
28: scanning progress status output unit
29, 29A, 29B, 29C: body controller
30: input device
31: three-dimensional ultrasound image acquisition unit
32, 32A, 32B, 32C: processor
41: pulser
42: amplifying unit
43: AD conversion unit
44: beam former
45: signal processing unit
46: DSC
47: image processing unit
51: optical camera
52: optical image analysis unit
53, 56: posture detection unit
54: pressure sensor
55: signal analysis unit
A1: right lobe
A2: left lobe
B: examination table
M1, M2: organ template
R1: region that has been scanned
R2: region that has not yet been scanned
S2 to S8: sub-section
T1: rear section
T2: front section
T3: inner section
T4: outer section

What is claimed is:

1. An ultrasound diagnostic apparatus for observing an organ of a subject by performing scanning using an ultrasound probe, the ultrasound diagnostic apparatus comprising:
a template memory in which a plurality of organ templates are stored; and
a processor configured to:
acquire a three-dimensional ultrasound image of the organ by transmitting and receiving an ultrasound beam using the ultrasound probe;
select one organ template from among the plurality of organ templates in accordance with a posture of the subject;
specify a scanning progress status of the ultrasound probe for the organ by performing registration between the three-dimensional ultrasound image and the one organ template; and
output the specified scanning progress status.

2. The ultrasound diagnostic apparatus according to claim 1,
wherein the plurality of organ templates include organ templates corresponding to the organ in respective cases in which the subject is in a sitting posture, a decubitus posture, a ventral decubitus posture, and a lateral decubitus posture.

3. The ultrasound diagnostic apparatus according to claim 1,
wherein each of the plurality of organ templates consists of three-dimensional data representing a contour of the organ in accordance with the posture of the subject.

4. The ultrasound diagnostic apparatus according to claim 2,
wherein each of the plurality of organ templates consists of three-dimensional data representing a contour of the organ in accordance with the posture of the subject.

5. The ultrasound diagnostic apparatus according to claim 1,
wherein each of the plurality of organ templates consists of three-dimensional data representing a contour of the organ and an internal structure of the organ in accordance with the posture of the subject.

6. The ultrasound diagnostic apparatus according to claim 2,
wherein each of the plurality of organ templates consists of three-dimensional data representing a contour of the organ and an internal structure of the organ in accordance with the posture of the subject.

7. The ultrasound diagnostic apparatus according to claim 1,
wherein the processor is configured to select the one organ template based on the posture of the subject designated by the user.

8. The ultrasound diagnostic apparatus according to claim 1, wherein the processor is configured to:

detect the posture of the subject; and select the one organ template based on the detected posture of the subject.

9. The ultrasound diagnostic apparatus according to claim 8, wherein the processor is configured to calculate a degree of similarity with respect to the detected posture of the subject for each of the plurality of organ templates, and selects an organ template having a highest degree of similarity as the one organ template.

10. The ultrasound diagnostic apparatus according to claim 8, wherein the processor is configured to select the one organ template by using a trained model that has learned the posture of the subject.

11. The ultrasound diagnostic apparatus according to claim 8, further comprising:

an optical camera configured to image the subject to acquire an optical image of the subject, and wherein the processor is configured to detect the posture of the subject by analyzing the optical image acquired by the optical camera.

12. The ultrasound diagnostic apparatus according to claim 8, further comprising:

at least one pressure sensor that is disposed on an examination table on which the subject is placed, and wherein the processor is configured to detect the posture of the subject by analyzing a detection signal acquired by the at least one pressure sensor.

13. The ultrasound diagnostic apparatus according to claim 1, wherein the processor is configured to select the one organ template based on the three-dimensional ultrasound image.

14. The ultrasound diagnostic apparatus according to claim 13, wherein the processor is configured to:

calculate a degree of similarity with respect to the three-dimensional ultrasound image for each of the plurality of organ templates; and select an organ template having a highest degree of similarity as the one organ template.

15. The ultrasound diagnostic apparatus according to claim 13, wherein the processor is configured to select the one organ template by using a trained model that has learned the three-dimensional ultrasound image of the organ in accordance with the posture of the subject.

16. The ultrasound diagnostic apparatus according to claim 1, further comprising:

a monitor, wherein the processor is configured to display the scanning progress status of the ultrasound probe on the monitor.

17. The ultrasound diagnostic apparatus according to claim 16, wherein the processor is configured to display a region that has been scanned using the ultrasound probe or a region that has not yet been scanned using the ultrasound probe on the monitor as the scanning progress status.

18. The ultrasound diagnostic apparatus according to claim 1, wherein the processor is configured to:

divide the organ into a plurality of sections;

quantify the scanning progress status of the ultrasound probe in each of the plurality of sections; and output the quantified scanning progress status.

19. The ultrasound diagnostic apparatus according to claim 18, wherein the processor is configured to outputs a section in which further scanning using the ultrasound probe is recommended among the plurality of sections based on the quantified scanning progress statuses of the ultrasound probe in the plurality of sections.

20. A method of controlling an ultrasound diagnostic apparatus for observing an organ of a subject by performing scanning using an ultrasound probe, the method comprising:

storing a plurality of organ templates in a template memory;

acquiring a three-dimensional ultrasound image of the organ by transmitting and receiving an ultrasound beam using the ultrasound probe;

selecting one organ template from among the plurality of organ templates in accordance with a posture of the subject; and specifying a scanning progress status of the ultrasound probe for the organ by performing registration between the acquired three-dimensional ultrasound image and the selected one organ template, and outputting the specified scanning progress status.

* * * * *